(12) United States Patent
Wilson (10) Patent No.: US 12,245,985 B1
(45) Date of Patent: Mar. 11, 2025

(54) APPARATUS FOR DRAWING MEDICINE FROM A MEDICINE CONTAINER TO A SYRINGE

(71) Applicant: James C. Wilson, Austin, TX (US)

(72) Inventor: James C. Wilson, Austin, TX (US)

(*) Notice: Subject to any disclaimer, the term of this patent is extended or adjusted under 35 U.S.C. 154(b) by 0 days.

(21) Appl. No.: 18/936,174

(22) Filed: Nov. 4, 2024

Related U.S. Application Data (60) Provisional application No. 63/547,226, filed on Nov. 3, 2023.

(51) Int. Cl.
*A61J 1/20* (2006.01)
*A61J 1/16* (2023.01)
*A61M 5/178* (2006.01)

(52) U.S. Cl.
CPC .............. *A61J 1/2003* (2015.05); *A61J 1/16* (2013.01); *A61J 1/20* (2013.01); *A61M 5/1782* (2013.01)

(58) Field of Classification Search
CPC ....... A61M 5/1782; A61M 5/14; A61J 1/2003
See application file for complete search history.

(56) References Cited

U.S. PATENT DOCUMENTS

| | | | |
|---|---|---|---|
| 3,907,009 A * | 9/1975 | Dobbins | A61M 5/1782 141/378 |
| 4,338,935 A | 7/1982 | Wilson | |
| 7,677,275 B2 | 3/2010 | Witte | |
| 9,671,060 B1 | 6/2017 | Cifers et al. | |
| D950,048 S | 4/2022 | Porkert | |
| 2008/0125722 A1 | 5/2008 | Knapp et al. | |
| 2020/0368448 A1 | 11/2020 | Shor et al. | |
| 2021/0308012 A1 * | 10/2021 | Tagliamento | A61J 1/2062 |
| 2024/0288885 A1 * | 8/2024 | Shem-Tov | A61J 3/002 |

FOREIGN PATENT DOCUMENTS

WO WO2023037163 A1 3/2023

OTHER PUBLICATIONS

Burke, Ashley et al.; Developing a 3D Food Printer; https://digital.wpi.edu/pdfviewer/kw52jc28w; Aug. 2022-Mar. 2023.
Halberg, Franz; A Precision-Measuring Adapter for Small-Volume Syringes; https://sci-hub.se/https://doi.org/10.1007/BF02174828; 1950.

* cited by examiner

*Primary Examiner* — Leslie R Deak
(74) *Attorney, Agent, or Firm* — HULSEY P.C.

(57) ABSTRACT

An apparatus for drawing medicine from a medicine container into a syringe is disclosed. The apparatus includes a base, and support frames extending from the base. The apparatus includes a top platform and a bottom platform. The bottom platform includes a fixed platform and a moveable platform. The moveable platform operably extends and retracts into the fixed platform along the support frames at the bottom of the fixed platform. The top platform positions above the bottom platform and receives a medicine container facing the bottom platform. The medicine container stores medicine. The fixed platform is configured to hold a flange of a syringe, and the moveable platform is configured to hold a plunger of the syringe. The moveable platform slides down from the fixed platform along the support frames engaging the plunger. The movement of the moveable platform draws medicine from the medicine container into the syringe.

20 Claims, 9 Drawing Sheets

APPARATUS FOR DRAWING MEDICINE FROM A MEDICINE CONTAINER TO A SYRINGE

CROSS-REFERENCE TO RELATED APPLICATIONS

The present application claims benefit of provisional Application No. 63/547,226, filed Nov. 3, 2023; all which is incorporated herein in its entirety and referenced thereto.

BACKGROUND OF THE INVENTION

Field of the Invention

The present invention relates to medical devices, and in particular, relates to an apparatus for connecting a syringe and a medicine container in order to draw medicine from the medicine container into the syringe.

Description of the Prior Art

It is known that medicinal fluids are administered to patients using a variety of methods. An exemplary method includes use of a syringe. The syringe includes a tube or barrel having a plunger and a needle. The syringe is used to administer the medicine to the patients. Some medical conditions require rapid delivery of the medicinal fluids. Traditionally, rapid infusion systems are used to deliver the medicinal fluids during resuscitation and/or hemorrhage, for example.

Several syringes or rapid infusion systems have been disclosed in the past. One such example is disclosed in a PCT Publication No. 2023037163, entitled "Infusion pump" ("the '163 Publication"). The '163 Publication discloses an infusion pump including automated syringe loading capabilities and/or medicinal fluid delivery capabilities to facilitate administration of medicinal fluids to a patient. The infusion pump may operate mechanically and may not require a power source to operate. The infusion pump may assist with filling a syringe with the medicinal fluid contents of one or more vials. The infusion pump may include a drug delivery assembly to deliver fluid at an adjustable but constant force. The infusion pump may permit the user to adjust the delivery rate continuously within a given range to improve comfort during infusion.

Another example is disclosed in a U.S. Pat. No. 4,338,935, entitled "Syringe support" ("the '935 Patent"). The '935 Patent discloses a syringe support having a horizontal body portion, a first bracket member for holding a syringe plunger head in position and a second bracket member for holding a syringe barrel while the support is clamped to a table. A patient may self-administer a medicinal dose contained in the syringe by placing a loaded syringe in the support and pressing his arm or other body portion against the needle of the syringe. Continued pressure against the needle causes injection by forcing the syringe barrel to slide along the support horizontal body portion in relation to the fixed piston or plunger until the cylinder abuts the second bracket member.

Another example is disclosed in a U.S. Pat. No. 7,677,275, entitled "One hand syringe filling device" ("the '275 Patent"). The '275 Patent discloses a device and method for easily filling a syringe with one hand. The device includes a flat hand for holding a medicine bottle, a syringe holder with a curved finger for holding a syringe, a mounted post for securing the device and a swivel arm mounted to the post which holds the flat hand, wherein the swivel arm allows the user to invert the flat hand and the medicine bottle secured therein, and easily draw medicine from the medicine bottle into the syringe with one hand.

Although the existing syringes or rapid infusion systems are useful, they have few problems. For example, the rapid infusion systems require the medical practitioner to exert a lot of energy to draw the medicine from the medicine container and administer the medicine to the patient. This leaves marks on the hands of the medical practitioner. Further, some of the syringes and the rapid infusion systems are bulky and complex to set up and use. Further, they take considerable time to operate.

Therefore, there is a need in the art to provide an apparatus for connecting a syringe and a medicine container in order to draw medicine from the medicine container into the syringe.

SUMMARY OF THE INVENTION

It is an object of the present invention to provide an apparatus for connecting a syringe and a medicine container for drawing medicine from the medicine container into the syringe and that avoids the drawback of known rapid infusion systems.

It is another object of the present invention to provide an apparatus for drawing medicine from a medicine container into a syringe with minimal physical exertion.

In order to achieve one or more objects, the present invention discloses an apparatus for drawing medicine from a medicine container into a syringe. The apparatus includes a base and support frames extending from the base. The apparatus includes a bottom platform connecting the support frames. The bottom platform includes a fixed platform and a moveable platform. The moveable platform operably extends and retracts into the fixed platform along the support frames at the bottom of the fixed platform. The apparatus includes poles extending from the fixed platform. The apparatus includes a top platform connecting the poles. The top platform positions above the bottom platform. The top platform receives a medicine container facing the bottom platform. The medicine container stores medicine.

The fixed platform is configured to hold the syringe facing the medicine container. Further, the moveable platform receives a plunger of the syringe. The moveable platform slides down from the fixed platform along said support frames engaging the plunger. The movement of the moveable platform draws medicine from the medicine container into the syringe.

In addition, the top platform includes first levers for slidably adjusting the position of the top platform along the poles. Further, the moveable platform includes second levers for controlling the movement of the moveable platform along the support members.

In one advantageous feature of the present invention, the apparatus helps a medical practitioner to connect the syringe and the medicine container to vertically positioned platforms in a secure manner. The top platform is adjusted vertically with respect to the fixed platform depending on the type and size of the medicine container. The bottom platform having a fixed second platform and a moveable third platform helps to connect the syringe. Here, the fixed second platform receives the flange of the syringe and the moveable third platform receives the plunger. After connecting, the medical practitioner pulls down the movable platform to engage the plunger to draw the medicine from the medicine container with minimal exertion. The apparatus presents an ergonomic design that prevents hand fatigue and makes it useful for repeated use.

In another advantageous feature of the present invention, the apparatus helps to connect different medicine containers such as bottles, pouches, etc., and connect the syringe to the medicine container to draw the medicine from the medicine container into the syringe.

In another advantageous feature of the present invention, the apparatus provides vertically positioned platforms, in which a fixed platform is positioned between a top platform and a moveable platform. Each of the top platform and the moveable platform has levers for locking their position over the poles and the support members, respectively. The precise locking allows control delivery of the medicine from the medicine container into the syringe.

The features and advantages of the invention here will become more apparent in light of the following detailed description of selected embodiments, as illustrated in the accompanying FIGURES. As will be realized, the invention disclosed is capable of modifications in various respects, all without departing from the scope of the invention. Accordingly, the drawings and the description are to be regarded as illustrative in nature.

DETAILED DESCRIPTION OF THE PREFERRED EMBODIMENT

The detailed description set forth below in connection with the appended drawings is intended as a description of exemplary embodiments in which the presently disclosed invention may be practiced. The term "exemplary" used throughout this description means "serving as an example, instance, or illustration," and should not necessarily be construed as preferred or advantageous over other embodiments. The detailed description includes specific details for providing a thorough understanding of the presently disclosed apparatus. However, it will be apparent to those skilled in the art that the presently disclosed invention may be practiced without these specific details. In some instances, well-known structures and devices are shown in functional or conceptual diagram form in order to avoid obscuring the concepts of the presently disclosed apparatus.

In the present specification, an embodiment showing a singular component should not be considered limiting. Rather, the invention preferably encompasses other embodiments including a plurality of the same component, and vice-versa, unless explicitly stated otherwise herein. Moreover, the applicant does not intend for any term in the specification to be ascribed an uncommon or special meaning unless explicitly set forth as such. Further, the present invention encompasses present and future known equivalents to the known components referred to herein by way of illustration.

Although the present invention describes an apparatus, it is to be further understood that numerous changes may arise in the details of the embodiments of the apparatus. It is contemplated that all such changes and additional embodiments are within the spirit and true scope of this invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the invention and are not intended to limit the scope of the invention.

Various features and embodiments of an apparatus for drawing medicine from a medicine container into a syringe or filling medicine into a syringe from a medicine container are explained in conjunction with the description of FIGS. 1-11.

Figure 1:
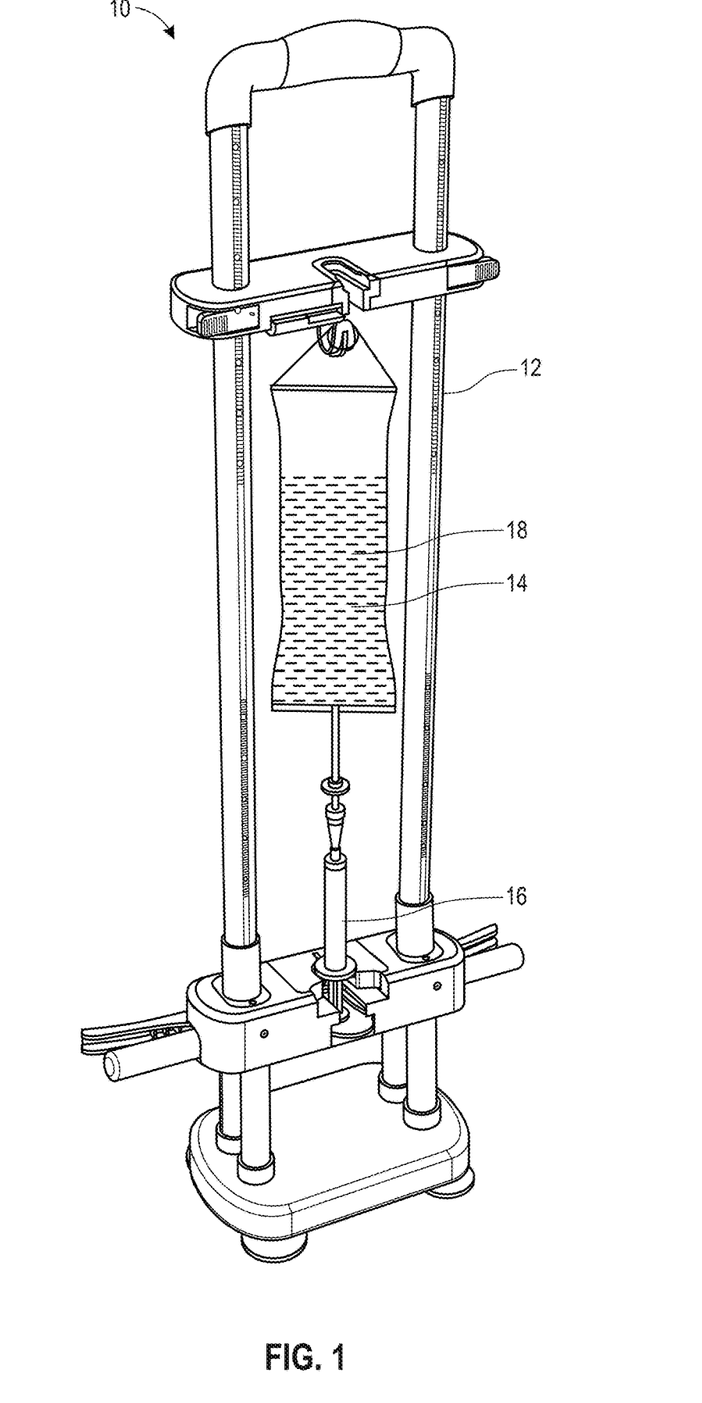
FIG. 1 is an environment of an apparatus for connecting a syringe to a medicine container, in accordance with one embodiment of the present invention.

FIG. 1 shows an environment 10 in which an apparatus 12 implements, in accordance with one embodiment of the present invention. Apparatus 12 positions over a surface such as a table or ground. Apparatus 12 receives a syringe 16 for drawing a medicine 18 from a medicine container 14. In one example, medicine container 14 includes an intravenous (IV) bag. In another example, medicine container 14 includes any medicine bag/pouch. Medicine 18 drawn from medicine container 14 is then used to administer medicine 18 to a patient (not shown) by a medical practitioner (not shown) using syringe 16.

Figure 2:
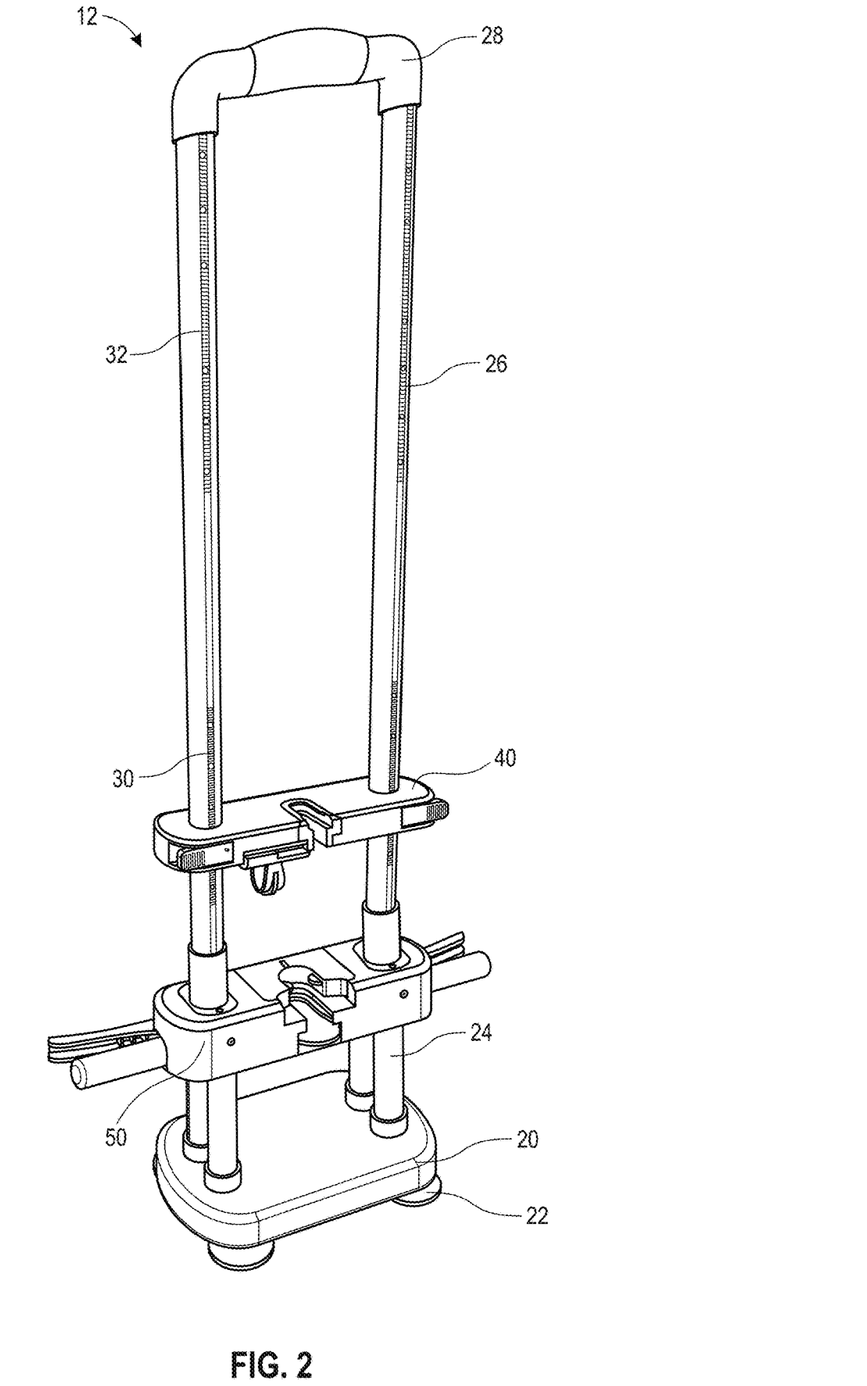
FIG. 2 is a perspective view of the apparatus, in accordance with one embodiment of the present invention.
Figure 3:
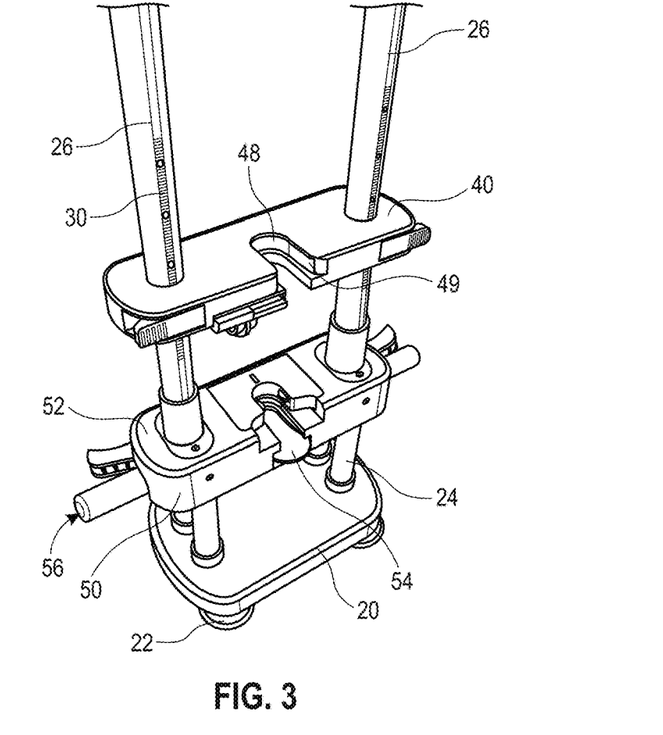
FIG. 3 is a closer partial perspective view of the apparatus showing platforms, in accordance with one embodiment of the present invention.
Figure 4:
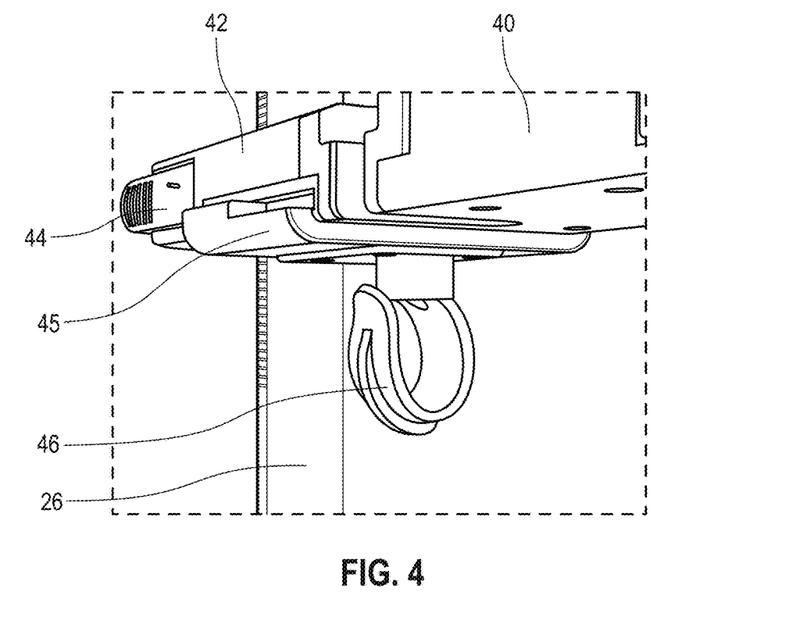
FIG. 4 is an enlarged view of a top/first platform, in accordance with one embodiment of the present invention.
Figure 5:
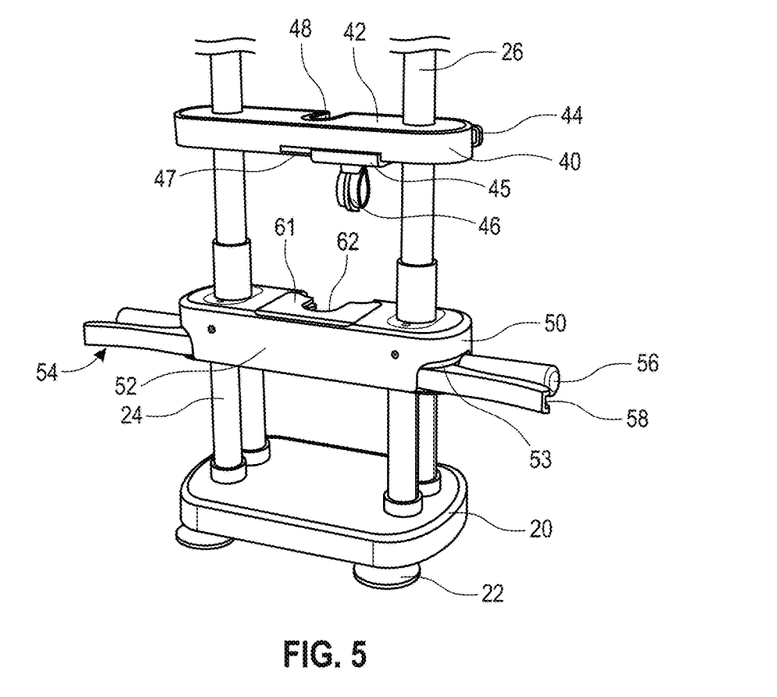
FIG. 5 is a partial rear view of the apparatus, in accordance with one embodiment of the present invention.

FIG. 2 shows a perspective view of apparatus 12, in accordance with one embodiment of the present invention. Apparatus 12 includes a base 20 having base support members 22. Base 20 is made up of a suitable material such as metal, plastic, wood, or any other suitable material. Base support members 22 act as legs and are made up of soft material to prevent damage to the surface. Base 20 includes support frames 24. Support frames 24 extend upwards from base 20. Further, apparatus 12 includes poles 26 extending from support frames 24 (bottom platform 50). In one example, support frames 24 include four elongated rods, in which a pair of them extend from each side of base 20. Further, poles 26 include two elongated rods, each of them extending from each side of base 20. As can be seen from FIG. 2, poles 26 encompasses a first platform or top platform 40 and support frames 24 encompass a bottom platform 50. Further, apparatus 12 includes a top frame 28 connecting poles 26 at the top. Top frame 28 connects opposite side poles 26 and operates as a handle, in some implementations. In one example, each of poles 26 comprises a first gripping portion 30 and a second gripping portion 32. First gripping portion 30 positions along a portion of the length of pole 26 at the bottom i.e., closer to fixed platform 50. Second gripping portion 32 positions along a portion of the length of pole 26 at the top i.e., closer to top frame 28.

Now referring to FIG. 1, FIG. 3, FIG. 4 and FIG. 5, constructional features of top platform or first platform 40 is explained, in accordance with one embodiment of the present invention. Top platform 40 includes a flat plate 42. Flat plate 42 connects to poles 26 and is made to slide along poles 26. Here, the position of top platform 40 along poles 26 can be locked either at first gripping portion 30 (FIG. 10) or at second gripping portion 32 (FIG. 1) in order to place top platform 40 at different heights from base 20 or bottom platform 50. Flat plate 42 encompasses first levers 44 positioned at sides. First levers 44 help to lock the position of top platform 40 along poles 26. Here, a user presses both first levers 44 to allow top platform 40 to slide up or down along poles 26. Upon reaching the desired position, the user releases first levers 44 to lock the position of top platform 40 along poles 26. It is preferable to connect/lock top platform 40 at either first gripping portion 30 or second gripping portion 32 such that top platform 40 remains in position and does not slide down when medicine container 14 is connected due to its weight. First plate 42 encompasses a sliding adapter 45. Sliding adapter 45 encompasses a hook member 46 extending down from first plate 42, as can be seen from at least FIG. 4.

Figure 10:
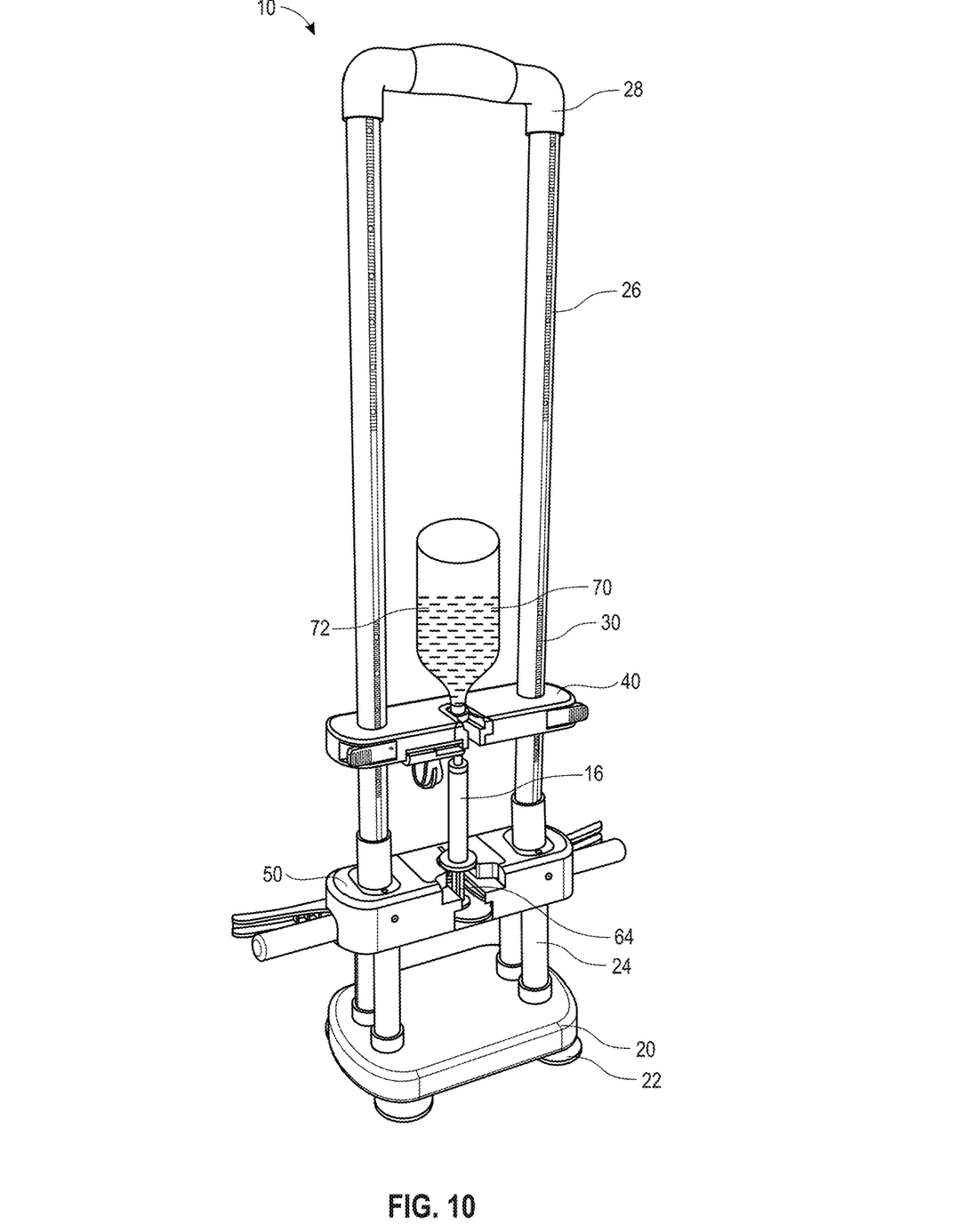
FIG. 10 and FIG. 11 illustrate operational features of the apparatus for drawing medicine from the medicine container, in accordance with another embodiment of the present invention.

In the present embodiment, first plate 42 encompasses a first cut section 48 at the center. First cut section 48 encompasses a first groove 49 that is configured to receive a neck of medicine container 70 (FIG. 10). Further, first plate 42 includes a slot 47 at the back i.e., opposite side of first cut section 48, as can be seen from FIG. 5. Slot 47 is provided offset to center and at the bottom of first plate 42 such that sliding adapter 45 is made to slide along slot 47. Sliding adapter 45 is made to slide to position hook member 46 at the center thereby blocking first cut section 48 in order to connect medicine container 14 to hook member 46 at the center, as shown in FIG. 1, for example. When another medicine container 70 such as a bottle needs to be connected, sliding adapter 45 is made to slide such that first cut section 48 is exposed and medicine container 70 can be inserted into first groove 49 at first cut section 48, as can be seen in FIG. 10, for example.

Figure 6:
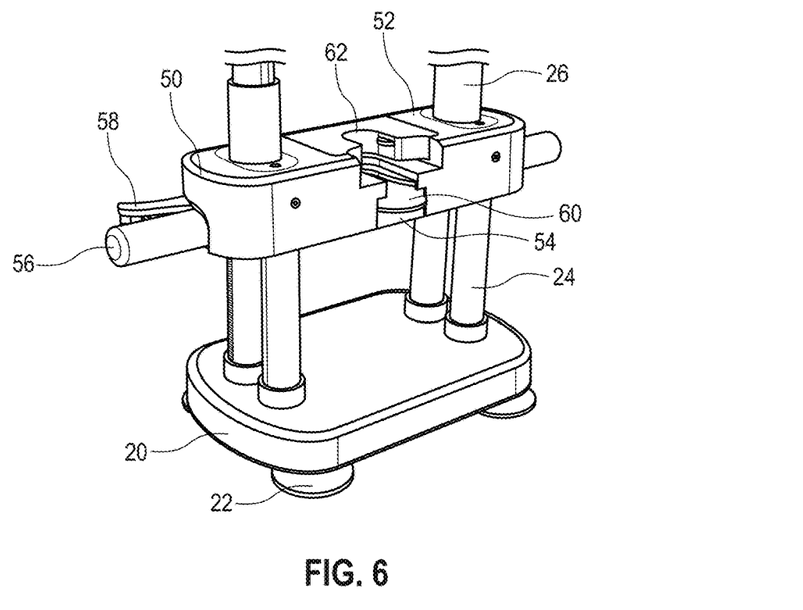
FIG. 6 is an enlarged view of a bottom platform having a fixed/second platform and a moveable/third platform, in accordance with one embodiment of the present invention.
Figure 7:
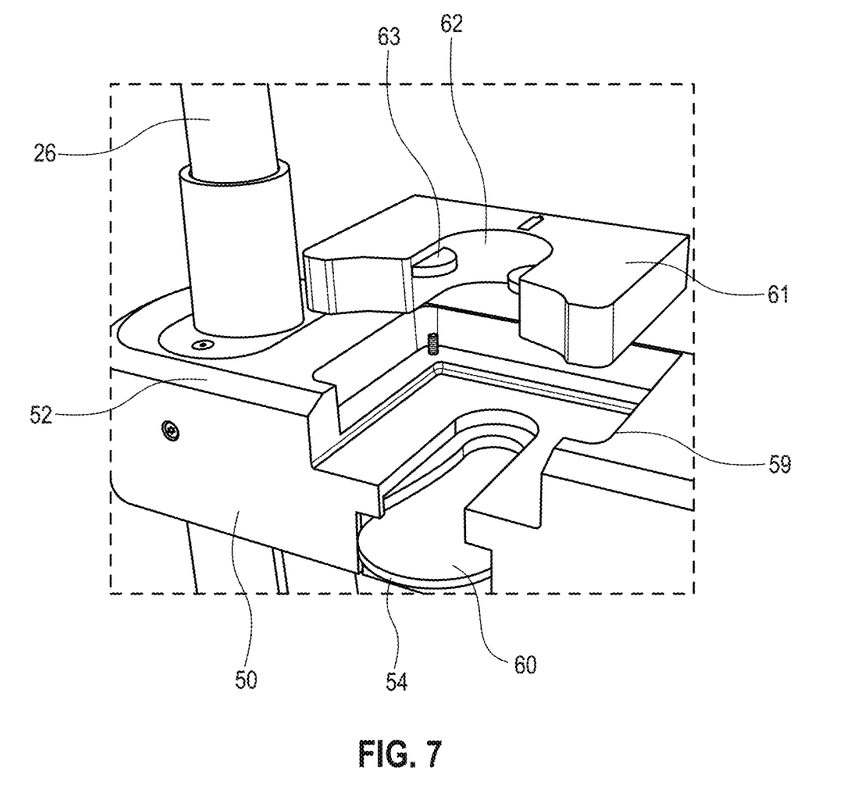
FIG. 7 is an exploded view of the fixed platform, in accordance with one embodiment of the present invention.
Figure 11:
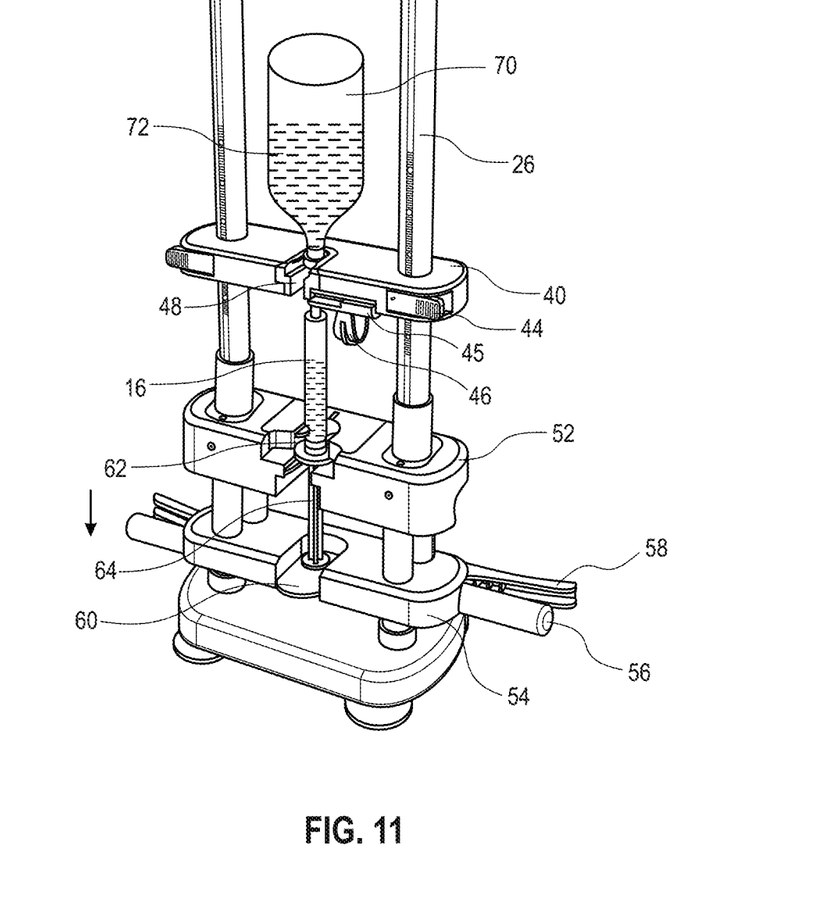

Bottom platform 50 includes a second platform 52 and a third platform 54. Referring to FIG. 6 and FIG. 7 (and FIG. 10), the constructional features of bottom platform 50 are explained. Second platform 52 positions below top/first platform 40. In one example, second platform 52 acts as a fixed platform and positions at a predefined height from base 20 with the help of support frames 24. For ease of reference, second platform 52 is referred to as fixed platform 52 hereinafter. Further, third platform 54 is referred to as moveable platform 54 hereinafter. Fixed platform 52 presents a platform receiving groove 53 (FIG. 5) at the bottom and operatively receives moveable platform 54 underneath. In other words, moveable platform 54 sits within fixed platform 52 and operatively extends from fixed platform 52 along support frames 24, as shown in FIG. 10, for example. In one implementation, moveable platform 54 encompasses second levers 56, 58. Second levers 56, 58 indicate handle brakes similar to bicycle brakes. Second levers 56, 58 extend from both sides of moveable platform 54. Here, second levers 56, 58 include a fixed lever 56 and an operative lever 58. The user operates operative levers 58 pushing against fixed levers 56 to disengage moveable platform 54, allowing moveable platform 54 to slide/move down from fixed platform 52 (FIG. 10) to the bottom of support frames 24 (FIG. 11). In one example, moveable platform 54 encompasses a third groove 60 for receiving a plunger 64 of syringe 16, as shown in FIG. 7. Third groove 60 allows plunger 64 to extend as moveable platform 54 is pulled/moved down from fixed platform 52 along support frames 24. In order to position moveable platform 54 into fixed platform 52, operative levers 58 are engaged against fixed levers 56. Subsequently, moveable platform 54 is pulled up along support frames 24 and into fixed platform 52 via platform receiving groove 53, as shown in FIG. 6, for example.

In one implementation, fixed platform 52 includes a block receiving slot 59 at the center, as shown in FIG. 7. Block receiving slot 59 receives a connecting block 61. Connecting block 61 includes a second cut-section 62 at the center. Second cut-section 62 aligns with first cut section 48 of top platform 40. Further, second cut-section 62 encompasses ridges 63. Ridges 63 extend from second cut-section 62 and help to connect a flange of syringe 16 to fixed platform 52.

Figure 8:
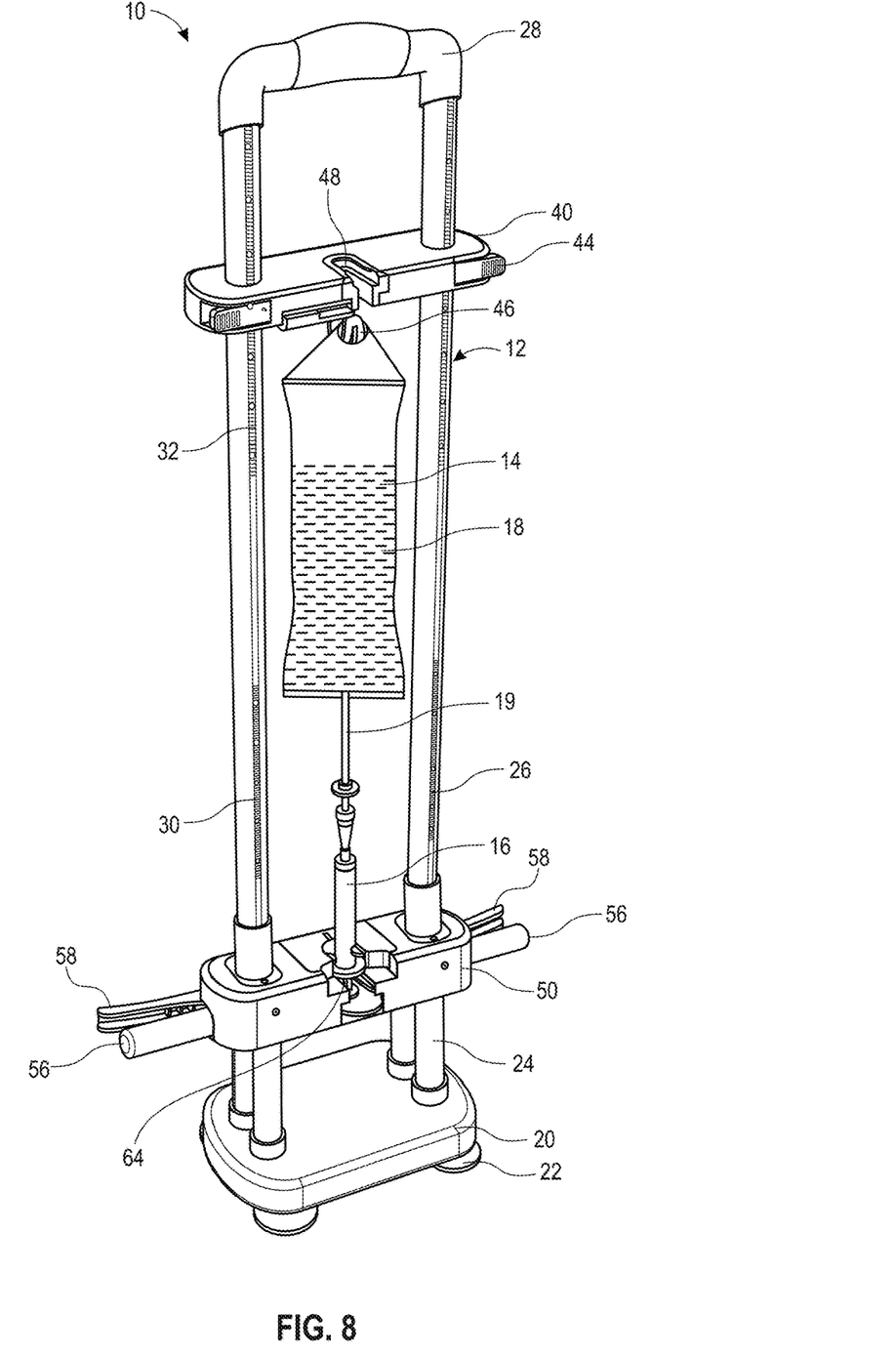
FIG. 8 and FIG. 9 illustrate operational features of the apparatus for drawing medicine from the medicine container, in accordance with one embodiment of the present invention.
Figure 9:
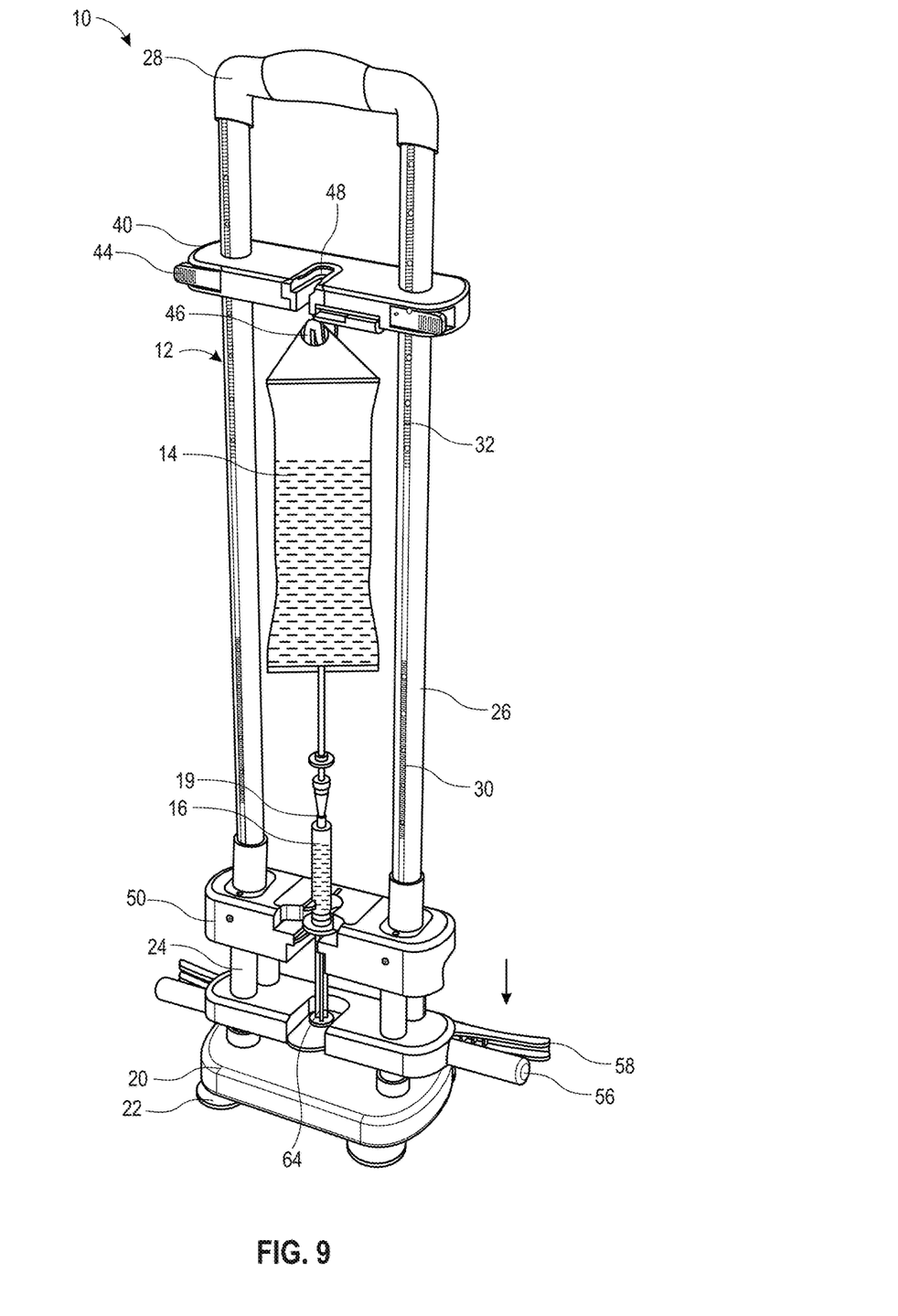

Now referring to FIG. 8 and FIG. 9, the operation of apparatus 12 for drawing medicine 18 from medicine container 14 into syringe 16 is explained, in accordance with one embodiment of the present invention. At first, medicine container 14 (medicine pouch) is connected to hook member 46. Here, sliding adapter 45 is made to slide to the center such that sliding adapter 45 covers first cut-section 48 and hook member 46 positions at the center. Subsequently, a flange of syringe 16 is made to slide into second cut-section 62 to connect syringe 16 facing upwards i.e., facing medicine container 14 suspending from hook member 46. Here, the flange rests against ridges 63 in second cut-section 62 (of fixed platform 52), and plunger 64 sits in third groove 60 of moveable platform 54 Subsequently, a needle 19 of syringe 16 is inserted into medicine container 14, as shown in FIG. 8. In order to draw medicine 18 into syringe 16, moveable platform 54 is made to slide down by operating second levers 56, 58, as shown in FIG. 9. Sliding/pulling down moveable platform 54 pulls down plunger 64 while fixed platform 52 holds the flange of syringe 16. This results in drawing medicine 18 from medicine container 14 into syringe 16. After drawing medicine 18, needle 19 is disconnected from medicine container 14 and syringe 16 is pulled out from fixed platform 52 and moveable platform 54.

Now referring to FIG. 10 and FIG. 11, the operation of apparatus 12 for drawing medicine 72 from a medicine container 70 into syringe 16 is explained, in accordance with another embodiment of the present invention. Here, medicine container 70 includes a medicine bottle. At first, the flange of syringe 16 is made to slide into second cut-section 62 to connect syringe 16 facing upwards i.e., facing medicine container 70. Here, the flange rests against ridges 63 in second cut-section 62 (of fixed platform 52), and plunger 64 sits in third groove 60 of moveable platform 54. Subsequently, sliding adapter 45 is pushed off center to expose first cut-section 48. Further, medicine container 70 is made to face upside down and the neck of medicine container 70 is inserted into first cut-section 48. Here, top platform 40 position is adjusted along poles 26 depending on the size of medicine container 70. In one example, top platform 40 is brought down to connect it at first gripping portion 30. Here, top platform 40 is slowly brought down by operating first levers 44 until the needle 19 of syringe 16 is inserted into medicine container 70, as shown in FIG. 10.

After inserting needle 19 into medicine container 70, moveable platform 54 is made to slide down (pulled down) by operating second levers 56, 58, as shown in FIG. 11. Sliding/pushing down moveable platform 54 pulls down plunger 64 while fixed platform 52 holds syringe 16. This results in drawing medicine 72 from medicine container 70 into syringe 16. After drawing medicine 72, top platform 40 is pushed up by operating first levers 44 to disconnect needle 19 from medicine container 70. Subsequently, syringe 16 is pulled out from fixed platform 52 and moveable platform 54. The above process is repeated for drawing medicine multiple times into the same or different syringes 16.

The presently disclosed apparatus provides several advantages over the prior art. The apparatus can be placed on a table or workbench or any other surface. The apparatus helps to slidably connect the syringe to the bottom platform and removably connect the medicine container to the top platform. The moveable/third platform is made to slide down/push down from the second/fixed platform to draw medicine from the medicine container into the syringe. The apparatus allows the user to simply connect the medicine container and the syringe, and manually pump the plunger via the moveable/third platform to draw the medicine. The apparatus is useful to nurses or medical practitioners who use syringes often. When compared to the prior art, the rapid infusion systems require the medical practitioner to exert a lot of energy to draw the medicine from the medicine container and administer the medicine to the patient. Further, this leaves marks on the hands of the medical practitioner. The presently disclosed apparatus avoids the medical practitioner from exerting a lot of energy to operate the syringe. In the present invention, the user can simply connect the medicine container to the top platform, and connect the syringe to the fixed/second platform and the moveable/third platform, and push down the moveable platform to pump/draw the medicine from the medicine container into the syringe. As the moveable platform holds the plunger, the user does not have to hold or exert energy. The user has to simply operate the second/handle levers at the moveable platform. This requires minimum physical exertion from the medical practitioner to draw the medicine into the syringe. As a result, the medical practitioner can operate the apparatus with ease. The apparatus can be used to clinics or hospitals for filling dosages multiple times. The apparatus can be referred to as a syringe aspirational volume efficiency (SAVE) device.

A person skilled in the art appreciates that the apparatus can come in a variety of shapes and sizes depending on the need and comfort of the user. Further, many changes in the design and placement of components may take place without deviating from the scope of the presently disclosed apparatus.

In the above description, numerous specific details are set forth such as examples of some embodiments, specific components, devices, methods, in order to provide a thorough understanding of embodiments of the present invention. It will be apparent to a person of ordinary skill in the art that these specific details need not be employed, and should not be construed to limit the scope of the invention.

In the development of any actual implementation, numerous implementation-specific decisions must be made to achieve the developer's specific goals, such as compliance with system-related and business-related constraints. Such a development effort might be complex and time-consuming, but may nevertheless be a routine undertaking of design, fabrication, and manufacture for those of ordinary skill. Hence as various changes could be made in the above constructions without departing from the scope of the invention, it is intended that all matter contained in the above description or shown in the accompanying drawings shall be interpreted as illustrative and not in a limiting sense.

The foregoing description of embodiments is provided to enable any person skilled in the art to make and use the invention. Various modifications to these embodiments will be readily apparent to those skilled in the art, and the novel principles and invention disclosed herein may be applied to other embodiments without the use of the innovative faculty. It is contemplated that additional embodiments are within the spirit and true scope of the disclosed invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus for drawing medicine from a medicine container into a syringe, said apparatus comprising:
a base;
support frames extending from said base;
a bottom platform connecting said support frames, wherein said bottom platform comprises a fixed platform and a moveable platform positioned at the bottom of said fixed platform, wherein said moveable platform operably extends and retracts into said fixed platform along said support frames at the bottom of said fixed platform;
poles extending upwards from said fixed platform; and
a top platform connecting said poles, wherein said top platform positions above said bottom platform, wherein said top platform receives a medicine container storing medicine,
wherein said medicine container connects to said top platform facing said bottom platform,
wherein said fixed platform is configured to hold a flange of a syringe, wherein said syringe connects to said medicine container,
wherein said moveable platform receives a plunger of said syringe,
wherein said moveable platform slides down from said fixed platform along said support frames engaging said plunger, and
wherein movement of said moveable platform draws medicine from said medicine container into said syringe.

2. The apparatus of claim 1, wherein said top platform comprises a slidable adapter having a hook member for receiving said medicine container.

3. The apparatus of claim 1, wherein said top platform comprises a first cut-section for receiving said medicine container.

4. The apparatus of claim 3, wherein said top platform comprises a slidable adapter having a hook member for receiving said medicine container, and wherein said slidable adapter slides horizontally and blocks said first cut-section exposing said hook member to connect said medicine container.

5. The apparatus of claim 1, wherein said top platform comprises first levers for slidably adjusting the position of said top platform along said poles.

6. The apparatus of claim 1, wherein each of said poles comprises gripping portions along its length to lock said top platform at various heights from said fixed platform.

7. The apparatus of claim 1, wherein said moveable platform comprises second levers for controlling the movement of said moveable platform along said support members.

8. The apparatus of claim 1, wherein said fixed platform comprises a second cut-section for holding said flange of said syringe in an upward position facing said top platform.

9. The apparatus of claim 8, wherein said second cut-section comprises ridges for holding said flange.

10. The apparatus of claim 1, wherein said moveable platform comprises a groove for receiving said plunger of said syringe.

11. An apparatus for drawing medicine from a medicine container into a syringe, said apparatus comprising:
a base;
support frames extending from said base;
a bottom platform connecting said support frames, wherein said bottom platform comprises a fixed platform and a moveable platform positioned at the bottom of said fixed platform, wherein said moveable platform operably extends and retracts into said fixed platform along said support frames at the bottom of said fixed platform; and
a top platform connecting said support frames, wherein said top platform positions above said fixed platform and receives a medicine container facing said bottom platform, and wherein said medicine container stores medicine,
wherein said fixed platform is configured to hold a flange of a syringe, and said moveable platform is configured to hold a plunger of said syringe,
wherein said moveable platform slides down from said fixed platform along said support frames engaging said plunger, and
wherein movement of said moveable platform draws medicine from said medicine container into said syringe.

12. The apparatus of claim 11, wherein said top platform comprises a slidable adapter having a hook member for receiving said medicine container.

13. The apparatus of claim 11, wherein said top platform comprises a first cut-section for receiving said medicine container.

14. The apparatus of claim 13, wherein said top platform comprises a slidable adapter having a hook member for receiving said medicine container, and wherein said slidable adapter slides horizontally and blocks said first cut-section exposing said hook member to connect said medicine container.

15. The apparatus of claim 11, wherein said top platform comprises first levers for slidably adjusting the position of said top platform along said support members, and wherein said moveable platform comprises second levers for controlling the movement of said moveable platform along said support members.

16. The apparatus of claim 11, wherein each of said support frames comprises gripping portions along its length to lock said top platform and said moveable platform at various heights from said fixed platform.

17. A method of drawing medicine from a medicine container into a syringe, said method comprising the steps of:
providing a base;
providing support frames extending from said base;
providing a bottom platform connecting said support frames, said bottom platform comprising a fixed platform and a moveable platform positioned at the bottom of said fixed platform, said moveable platform operably extending and retracting into said fixed platform along said support frames at the bottom of said fixed platform;
providing a top platform connecting said support frames;
positioning said top platform above said fixed platform and receiving a medicine container facing said bottom platform, said medicine container storing medicine;
connecting a flange of a syringe at said fixed platform;
connecting a plunger of said syringe at said moveable platform; and
pushing down said moveable platform from said fixed platform along said support frames engaging said plunger such that the movement of said moveable platform draws medicine from said medicine container into said syringe.

18. The method of claim 17, further comprising:
providing a first cut-section for receiving said medicine container at said top platform; or
providing a slidable adapter having a hook member for receiving said medicine container at said top platform, such that said slidable adapter slides horizontally and blocks said first cut-section exposing said hook member to connect said medicine container.

19. The method of claim 17, further comprising:
providing first levers for slidably adjusting the position of said top platform along said support members; and
providing second levers for controlling the movement of said moveable platform along said support members.

20. The method of claim 17, further comprising providing gripping portions along the length of said support frames to lock said top platform and said moveable platform at various heights from said fixed platform.

* * * * *